United States Patent [19]

Gipson et al.

[11] Patent Number: 4,922,894
[45] Date of Patent: May 8, 1990

[54] CERVICAL FASCIA RELEASE BOARD

[76] Inventors: Carey D. Gipson, 14344 Centreport Landing Cir., Apt. 1906, Fort Worth, Tex. 76155; James T. Jernigan, Rte. 2, Box 68-A, China Spring, Tex. 76633

[21] Appl. No.: 106,540
[22] Filed: Oct. 9, 1987
[51] Int. Cl.⁵ ............................................. A61F 5/04
[52] U.S. Cl. ..................................... 128/71; 128/69
[58] Field of Search ................. 128/69, 70, 71, 72, 128/73, 74

[56] References Cited

U.S. PATENT DOCUMENTS

| | | | |
|---|---|---|---|
| 712,375 | 10/1902 | Hartford | 128/69 |
| 1,437,568 | 12/1922 | Taplin | 128/70 |
| 1,549,601 | 8/1925 | Mulgrew | 128/69 |
| 1,904,039 | 4/1933 | Bruder | 128/69 |
| 2,534,587 | 12/1950 | Fisher et al. | 128/71 |
| 2,684,064 | 7/1954 | Thompson | 128/69 |
| 2,700,779 | 2/1955 | Tolkowsky | 128/70 |
| 3,621,839 | 11/1971 | Barthe | 128/69 |
| 3,753,264 | 8/1973 | Grenier | 128/71 |
| 4,114,612 | 9/1978 | Benjamin | 128/69 |
| 4,157,088 | 6/1979 | Gracey | 128/70 |
| 4,508,109 | 4/1985 | Saunders | 128/69 |
| 4,660,549 | 4/1987 | Kowalski et al. | 128/69 |
| 4,777,678 | 10/1988 | Moore | 128/69 |

FOREIGN PATENT DOCUMENTS

| | | | |
|---|---|---|---|
| 2630439 | 9/1977 | Fed. Rep. of Germany | 128/70 |
| 1347606 | 11/1963 | France | 128/69 |
| 1499275 | 9/1967 | France | 128/70 |
| 2260986 | 10/1975 | France | 128/70 |
| 2388548 | 12/1978 | France | 128/69 |
| 122883 | 2/1919 | United Kingdom | 128/69 |

Primary Examiner—Edgar S. Burr
Assistant Examiner—Tonya Lamb
Attorney, Agent, or Firm—Banner, Birch, McKie & Beckett

[57] ABSTRACT

A cervical fascia release board is provided to help relieve tension or tightness in the muscles in the head and neck area of the user. The board is formed of a base which includes a back rest area for the user and upstanding head/neck area and head supports attached to the base. The board is used by resting the occipital portion of the head and neck area on one support and as the muscles relax, the head gradually tilts back to rest on the other support. The head support is adjustable to the individual needs of the user.

18 Claims, 2 Drawing Sheets

CERVICAL FASCIA RELEASE BOARD

BACKGROUND OF THE INVENTION

The present invention relates to the field of medical therapy and more particular, is directed to a cervical fascia release board for the release of tension in muscles and connective tissue in the cervical region of humans.

SUMMARY OF THE INVENTION

Applicant's invention of the Cervical Fascia Release Board is an original and unique device designed to help relieve tension or tightness of the posterior muscles and fascia of the upper neck. The way this is done is by the patient laying on the device with the release board striking the neck approximately ½ inch off the occipital bone. The patient stays on the board between 90 to 120 seconds with all the resistance being applied by the weight of the head. The head will start tilting back during the treatment which is a result of the releasing of the muscles and fascia in this area. The first time the patient uses the board, someone should help set the release adjuster so that when his/her muscles are completely relaxed the head can rest on the adjuster. This enables the patient to have an idea of the placement of the head following the treatment and a further idea of the time span it takes to reach this release.

The Cervical Fascia Release Board can serve many functions in the medical, as well as chiropractic, field. One of these functions is to relax the muscles and fascia that attach to the occipital bone of the skull. This allows the release of tension and pressure in this area. The release of these muscles and fascia also help to relieve the pressure on the cervical vertebrae which in turn allows the vertebral foramen to widen taking pressure off the cervical nerves traveling through this foramen. Due to the decrease in pressure applied on the skull and vertebrae, there is an increase in the flow of cerebral spinal fluid through this area also.

Another function of Applicant's invention would provide to be beneficial for cervical traction. When a patient is placed in a traction device, the muscles and fascia are generally tight. As the treatment of traction begins, the automatic response of the muscles is to further tighten. If the patient was first placed on the Cervical Fascia Release Board and the muscles and fascia were allowed to relax, traction could then be initiated with maximal benefits. Another realm that the Cervical Fascia Release Board could be utilized in is the chiropractic field. It could greatly facilitate the muscular relaxation prior to the adjustment to the cervical region.

Fascia release is not a new technique, however, the use of this board would greatly assist the releasing treatment. In the past this treatment has been done manually by a therapist placing his/her fingertips just under the occipital bone. This is continued until the head releases. This is not only time consuming for the therapist, but causes discomfort to the hands and fingertips if done on patients routinely. The Cervical Fascia Release Board would eliminate both the time factor and the discomfort to the therapist.

DESCRIPTION OF THE PREFERRED EMBODIMENT

Figure 1:
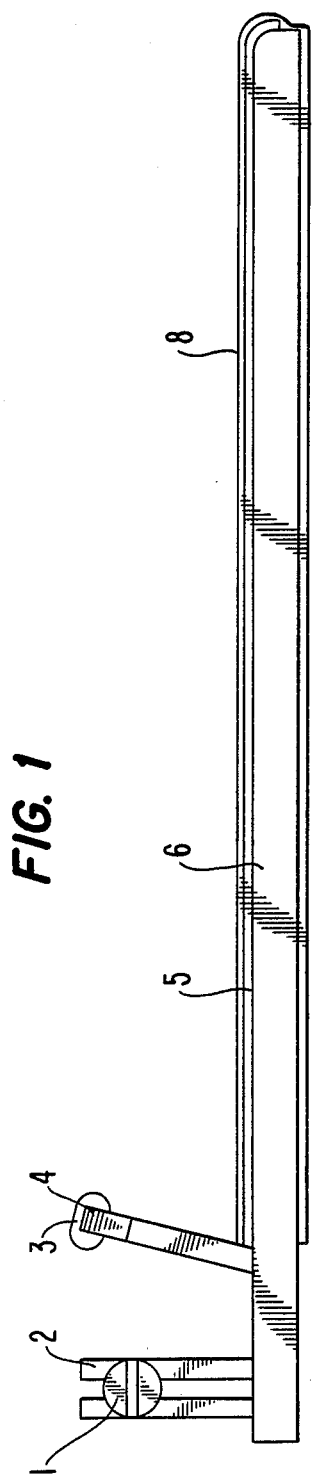
FIG. 1 is a side elevation view of a cervical fascia release board in accordance with Applicants' invention.
Figure 2:
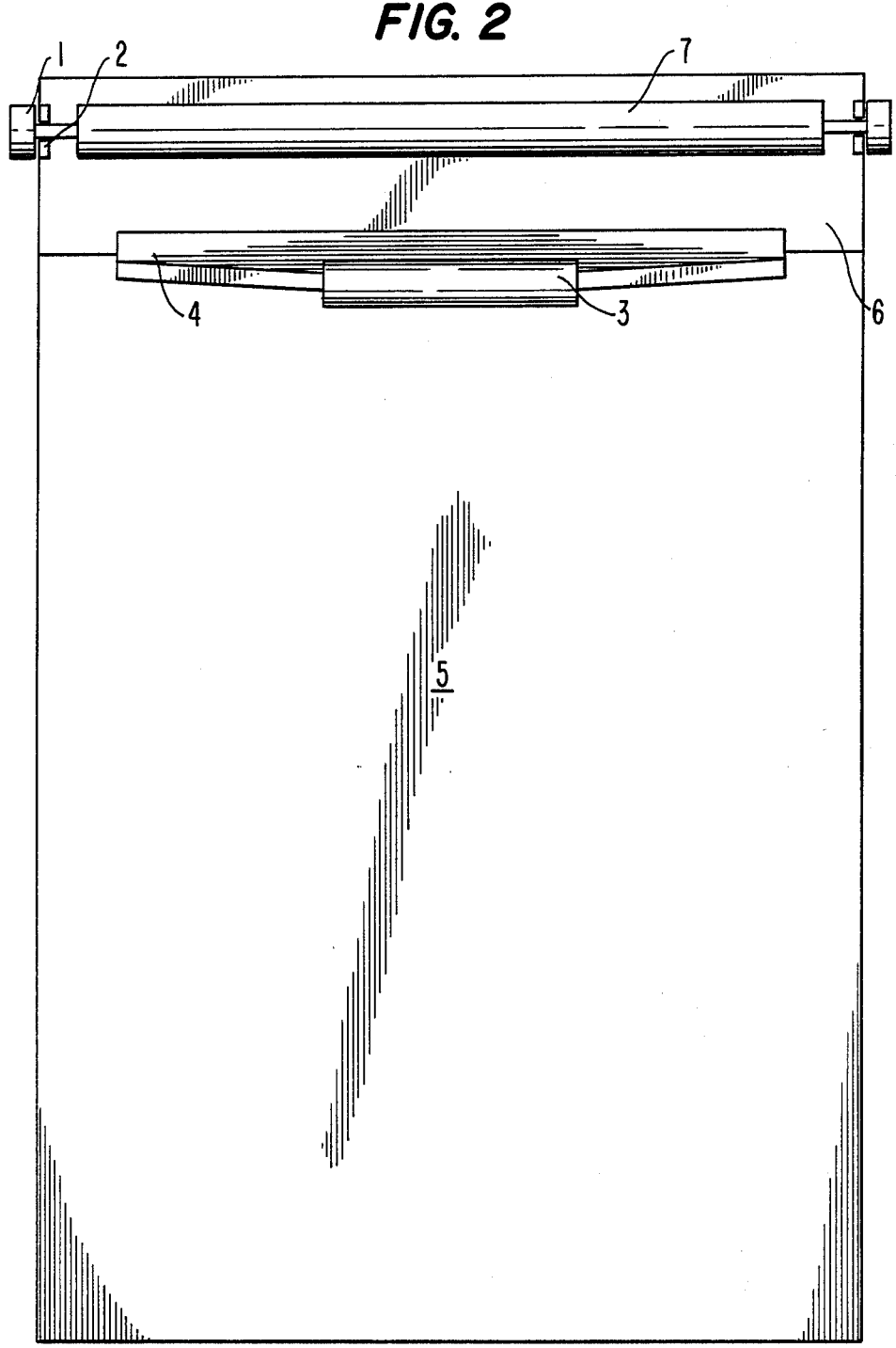
FIG. 2 is a top plan view of a cervical fascia release board according to Applicants.

Though FIGS. 1 and 2 are drawn to a scale of ⅜" to 1" and show dimensions which Applicants' have found to be successful in the practice of the invention, the invention is not limited to the particular dimensions shown.

Reference No. 1 refers to a ¼" bolt with wingnut which is used to tighten down the release adjuster. Reference No. 2 refers to a guidepost for the release adjuster. Reference No. 3 refers to padding that conforms to the release board. Reference No. 4 refers to the actual release board that is placed just under the occipital bone. Reference Nos. 5 and 8 refer to the foam rubber and vinyl covering over the base board. Reference No. 6 refers to the base board. Reference No. 7 refers to the metal piece that makes up the release adjuster.

The construction of applicants' Cervical Fascia Release Board begins by setting up the base board 6. This board is a piece of ¾" plywood which measures 2 feet by 16 inches. The base board is designed to stabilize the patient during the treatment. Foam rubber 5 is then laid on the board only covering the area from the release board down. This is applied for the purpose of maximal comfort to the patient. A vinyl covering 8 is then applied over the entire base board to stabilize the foam rubber and enhance appearance.

The next step followed is the attachment of the release board 4 to the base board. The release board is a piece of plywood ¾ inch by 13 inches. This piece of plywood does not run straight across, but has been sanded down in the following manner. The middle 5 inches of the release board stands 3 inches from base to top, it has then been sanded down to 2¼ inches for the remaining width of the release board. The purpose of this angling is concerned with the area of the neck being struck by the board. An area of 5 inches is maximal for the benefits of muscular and connective tissue relaxation. The release board is then attached to the base board 3 inches from the top at an angle 75° from the horizontal plane. The top of the release board is directed into the area just under the occipital bone when the patient lays down on the board. The attachment of the release board at an angle allows the musculature and connective tissue to release. If the board were not angled, the board would compress into the occipital bone instead of allowing the release to occur. The final step to the release board is the attachment of padding 3 for the purpose of comfort to the patient.

The release adjuster 7 can now be attached to the base board. Two 3 inch metal guideposts 2 with ¼ inch slits down the middle are attached to the base board. These metal guide-posts are attached to the base board with two ½" wood screws. The release adjuster, which is 14½ in length, 1" in width, and ⅛" in thickness, is then attached to the metal guidepost with ¼ inch bolts with wingnuts 1. The purpose of the release adjuster is the determination of the completion of the treatment.

We claim:

1. A device for relieving muscle tension in the head and neck area of a user, said device comprising:
   a substantially flat base having a top end and a bottom end;
   a first support member attached to said base and extending upwardly therefrom, said first support member providing support for the head and neck area of the user thereby causing release of the muscles of the head and neck area; and a second support member attached to said base between said top end and said first support member and extending upwardly therefrom, said second support member supporting the head of the user only after the muscles have been released, said second support member including adjustable head support means for adjusting the support position of the second support member.

2. The device of claim 1, wherein said first support member extends upward from said base at an angle less than 90°.

3. The device of claim 1, wherein said angle is 75°.

4. The device of claim 1, wherein said first support member includes pad means for providing a cushion between said first support member and the head and neck area of the user.

5. The device of claim 1, wherein said first support member is formed of a single member positioned across said base and having an upward edge which includes a support edge for supporting the head and neck area of the user, said support edge comprising less than the entire upward edge of said single member.

6. The device of claim 1, wherein said second support member is spaced apart from said first support member.

7. The device of claim 1, wherein said second support member extends substantially perpendicular to said base.

8. The device of claim 7, wherein said second support member is formed of spaced apart and upwardly extending first and second extensions and a head support mounted between said first and second extensions.

9. The device of claim 8, wherein said adjustable head support means includes respective elongated openings in said first and second extensions, respective ends of said head support being received in said openings and being fixed thereto with releasable fastening means.

10. The device of claim 9, wherein said releasable fastening means is formed of at least one nut and a corresponding bolt.

11. The device of claim 1, wherein a portion of said base forms a back rest portion for supporting the back of a user when said device is being used.

12. The device of claim 11, wherein said back rest portion includes a cushion between said base and the back of the user.

13. The device of claim 12 including covering means for covering said base and said cushion.

14. A device for relieving muscle tension in the head and neck area of a user, said device comprising:

a substantially flat base having a top end and a bottom end, said base having a cushioned back support area for supporting the back of the user while using said device;

a first support member attached to said base and extending upwardly therefrom at an angle with respect to said base of about 75 degrees, said first support member providing cushioned support for the head and neck area of the user thereby causing release of the muscles of the head and neck area; and a second support member spaced apart from said first support member and attached to said base between said top end and said first support member, said second support member extending upwardly therefrom and being substantially perpendicular to said base, said second support member supporting the head of the user only after the muscles have released, said second support member including adjustable head support means for adjusting the support position of the second support member.

15. The device of claim 14, wherein said first support member is formed of a single member positioned across said base and having an upward edge which includes a support edge for supporting the head and neck area of said user, said support edge comprising less than the entire upward edge of said single member.

16. The device of claim 14, wherein said adjustable head support means includes respective elongated openings in first and second upstanding extensions, respective ends of a head support being received in said opening and being fixed thereto with releasable fastening means.

17. The device of claim 16, wherein said releasable fastening means is formed of at least one nut and a corresponding bolt.

18. The device of claim 14 including covering means for covering at least a portion of said base.

* * * * *